United States Patent [19]
Eggler et al.

[11] 3,984,400
[45] Oct. 5, 1976

[54] 11-DESOXY-16-ARYL-ω-TETRANORPROSTAGLANDINS

[75] Inventors: James F. Eggler, Stonington; Jasjit S. Bindra, Groton; Hans-Jurgen E. Hess, Old Lyme, all of Conn.

[73] Assignee: Pfizer Inc., New York, N.Y.

[22] Filed: Oct. 21, 1975

[21] Appl. No.: 624,486

[52] U.S. Cl. .................. 260/240 R; 260/468 D; 260/346.2 R
[51] Int. Cl.$^2$ .................................. C07C 177/00
[58] Field of Search ............ 260/240 R, 346.2 R, 260/468 D

[56] References Cited
UNITED STATES PATENTS

| | | | |
|---|---|---|---|
| 3,840,573 | 10/1974 | Jung et al. | 260/468 D X |
| 3,932,389 | 1/1976 | Johnson et al. | 260/240 R |

OTHER PUBLICATIONS

Gandolfi, C., et al., Farmaco [Sci] 27:1125 (1972), (Upjohn Card Index No. 1405).
Pappo, R., et al., Tetrahedron Lett.: 2627 (1972), (Upjohn Card Index No. 1164).
Corey, E. J., et al., Tetrahedron Lett.: 311 (1970), (Upjohn Card Index No. 855).

*Primary Examiner*—Allen B. Curtis
*Attorney, Agent, or Firm*—Connolly and Hutz

[57] ABSTRACT

11-Desoxy-16-aryl-ω-tetranorprostaglandins and various intermediates and processes employed in their preparation are disclosed. The novel prostaglandins of this invention have been found to have activity profiles comparable to the parent prostaglandins but they exhibit a greater tissue specificity of action.

4 Claims, No Drawings

11-DESOXY-16-ARYL-ω-TETRANORPROSTA-GLANDINS

BACKGROUND OF THE INVENTION

This invention relates to certain novel analogs of the naturally occurring prostaglandins, synthetic intermediates and processes employed in their preparation. In particular, it relates to novel 11-desoxy-13,14-dehydro-16-aryl-ω-tetranor-prostaglandins of the $E_2$ and $F_2$ series.

The prostaglandins are C-20 unsaturated fatty acids which exhibit diverse physiological effects. Each of the known, naturally occurring prostaglandins is derived from prostanoic acid which has the structure and position numbering:

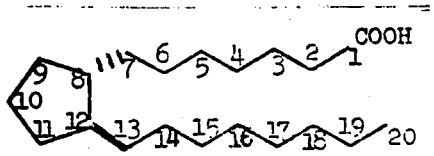

[Bergstrom et al., Pharmacol. Rev. 20, 1 (1968), and references cited therein.] A systematic name for prostanoic acid is 7-[(2β-octyl)-cyclopent-1α-yl]heptanoic acid.

$PGA_2$ has the structure:

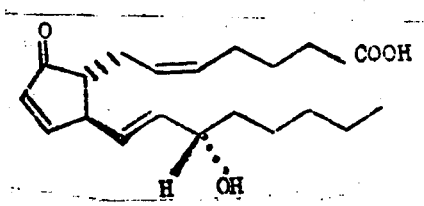

$PGB_2$ has the structure:

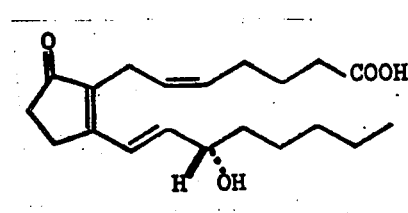

$PGE_2$ has the structure:

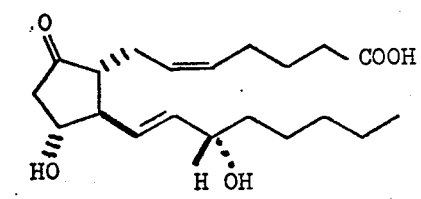

$PGF_{2\alpha}$ has the structure:

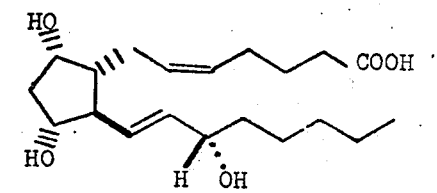

$PGF_{2\beta}$ has the structure:

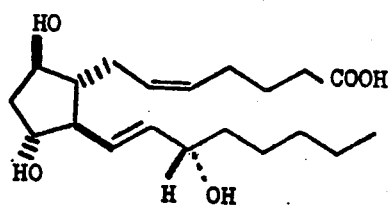

Each of the $PG_1$ prostaglandins, $PGE_1$, $PGF_{1\alpha}$, $PGF_{1\beta}$, $PGA_1$, and $PGB_1$, has a structure the same as the corresponding $PG_2$ compound except that the cis double bond between C-5 and C-6 is replaced by a single bond. For example, $PGA_1$ has the structure:

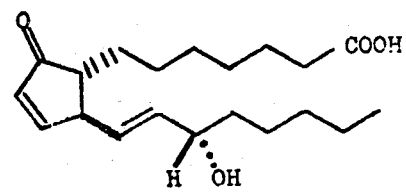

The $PG_0$ compounds are those in which there are no double bonds in either side chain. For instance, $PGE_0$ has the structure

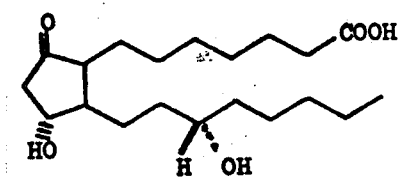

Broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

The side-chain hydroxy at C-15 in the above formulas is in S configuration. [See, Nature, 212, 38 (1966) for discussion of the stereochemistry of the prostaglandins.]

Molecules of the known prostaglandins each have several centers of asymmetry, and can exist in racemic (optically inactive) form and in either of the two enantiomeric (optically active) forms, i.e. the dextrorotatory and levorotatory forms. As drawn above, each structure represents the particular optically active form of the prostaglandin which is obtained from certain mammalian tissues, for example, sheep vesicular glands, swine lung, or human seminal plasma, or by carbonyl and/or double bond reduction of that prostaglandin. [Bergstrom et al., cited above.] The mirror image or optical antipode of each of the above structures represents the other enantiomer of that prostaglandin. For instance, the optical antipode of PGF$_2\alpha$ (ent-PGF$_2\alpha$) is drawn as

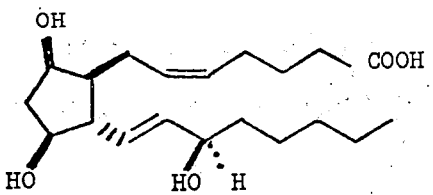

The racemic form of a prostaglandin contains equal numbers of a particular stereoisomer and its mirror image. When reference to a prostaglandin racemate is intended, the symbols "rac" or "dl" will precede the prostaglandin name. Two structures are needed to represent a racemate. For instance, the structure of dl-PGF$_2\alpha$ is properly represented as an equimolar mixture of PGF$_2\alpha$ and ent-PGF$_2\alpha$. The terms PGE$_1$, PGE$_2$, PGF$_{1\alpha}$ and the like as used herein will mean that stereoisomer with the same absolute configuration as the corresponding prostaglandin found in mammalian tissue.

In an otpical antipode, the absolute configuration at all of the above-mentioned centers of asymmetry is inverted. In an epimer, the configuration is inverted at one or more but not all of the centers. For instance, the absolute configuration of the 15-hydroxy group in 15-epi-PGF$_2\alpha$ is the R configuration and is shown as

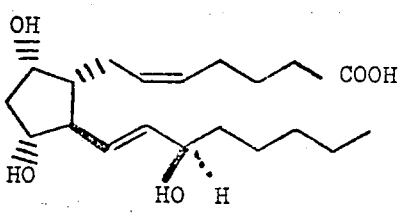

It will be noted that only the configuration at the 15-position is inverted and that at the other centers of asymmetry, namely the 8-, 9-, 11- and 12-positions, the absolute configuration is the same as that in the naturally-occurring mammalian PGF$_2\alpha$. Racemic mixtures of epimers may also exist for instance, if 15-keto-PGF$_2\alpha$ is reduced with zinc borohydride or a hindered alkyl borohydride, the resulting product is a racemic mixture of 15$\alpha$-hydroxy and 15$\beta$-hydroxy-PGF$_2\alpha$.

PGE$_1$, PGE$_2$, and the corresponding PGF$\alpha$, PGF$\beta$, PGA, and PGB compounds, and many of their derivatives such as the esters, acylates, and pharmacologically acceptable salts, are extremely potent inducers of various biological responses. These compounds are, therefore, potentially useful for pharmacological purposes. [Bergstom et al, cited above.] A few of those biological responses are systemic arterial blood pressure lowering in the case of the PGE, PGF $\beta$ and PGA compounds as shown in cardiac cannulated rats or dogs; pressor activity for the PGF $\alpha$ compounds; stimulation of smooth muscle as shown by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decrease of blood platelet adhesiveness as shown by platelet-to-glass adhesiveness, and inhibition of blood platelet aggregation and thrombus formation induced by various physical stimuli, e.g., arterial injury; and in the case of the PGE and PGB compounds, stimulation of epidermal proliferation and keratinization as shown when applied in culture to embryonic chick and rat skin segments.

Prostaglandins are useful to prevent, control, or alleviate a wide variety of diseases and undesirable physiological conditions in avians and mammals, including humans, useful domestic animals, pets, and zoological specimens, and in laboratory animals, for example, mice, rats, rabbits, and monkeys.

For example, these compounds, especially those of the E series, are useful in mammals, including man, as bronchodilators [Cuthbert, Brit. Med. J., 4: 723-726, 1969]. As nasal decongestants, the compounds are used in a dose range of about 10 $\mu$g. to about 10 mg. per ml. of a pharmacologically suitable liquid vehicle or as an aerosol spray, both for topical application.

The PGE compounds are useful in the treatment of asthma because of their activity as bronchodilators and/or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of routes in a number of dosage forms, e.g., orally in the form of tablets, capsules, or liquids; rectally in the form of suppositories; parenterally with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day. These prostaglandins can also be combined advantageously with other antiasthmatic agents, such as sympathomimetics (isoproterenol, phenylephrine, ephedrine, etc.); xanthine derivatives (theophylline and aminophyllin); and cortiscosteroids (ACTH and predinisolone). Regarding use of these compounds see South African Patent No. 68/1055.

The PGE and PGA compounds are useful in mammals, including man and animals to reduce and control excessive gastric secretion, thereby reducing or avoiding gastrointestinal ulcer formation, and accelerating the healing of such ulcers already present in the gastrointestinal tract. [Shaw and Ramwell, In: Worchester Symposium on Prostaglandins, Wiley (New York, 1968), pp. 55-64.] For this purpose, the compounds are administered parenterally by injection or intravenous infusion in an infusion dose range of about 0.1 $\mu$g. to about 500 $\mu$g. per kg. of body weight per minute, or in a total daily dose by injection or infusion in the range of about 0.1 to about 20 mg. per kg. of body weight per day.

The PGE compounds are useful whenever it is desired to inhibit platelet aggregation, to reduce the adhesive character of platelets, and to remove or prevent the formation of thrombi in mammals, including man, rabbits, and rats. [Emmons et al., Brit. Med. J., 2: 468–472, 1967.] These compounds are, for example, useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically. For rapid response, especially in emergency situation, the intravenous route of administration is preferred. Doses in the range of about 0.005 to about 20 mg. per kg. of body weight per day are used.

The PGE compounds are especially useful as additives to blood, blood products, blood substitutes, and other fluids which are used in artifical extracorporeal circulation and perfusion of isolated body portions, e.g., limbs and organs, whether attached to the original body, detached and being preserved or prepared for transplant, or attached to the new body. Under such conditions, aggregated platelets tend to block the blood vessels and portions of the circulation apparatus. Such aggregation is inhibited by the presence of a prostaglandin. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter or circulating fluid.

PGE and PGF compounds are extremely potent in causing stimulation of smooth muscle, and are also highly active in potentiating other known smooth muscle stimulators. Therefore, $PGE_2$, for example, is useful in place of or in combination with less than usual amounts of these known smooth muscle stimulators, for example, to relieve the symptoms of paralytic ileus, or to control to prevent atonic uterine bleeding after abortion or delivery, to aid in expulsion of the placenta, and during the pueroperium. For the latter purpose, the PGE compound is administered intravenously immediately after abortion or delivery at a dose in the range of about 0.01 to about 50 µg. per kg. of body weight per minute until the desired effect is obtained. Subsequent doses are given parenterally during puerperium in the range 0.01 to 2 mg. per kg. of body weight per day.

The PGE, PGA and $PGF_\beta$ compounds are useful as hypotensive agents and vasodilators [Bergstrom et al., Acta Physiol. Scand., 64: 332–333, 1965; Life Sci., 6:449–455, 1967] in mammals, including man. To lower systemic arterial blood pressure, the compounds are administered by intravenous infusion at the rate of about 0.01 to about 50 µg. per kg. of body weight per minute, or in single or multiple doses of about 25 to 500 µg. per kg, of body weight total per day. [Weeks and King, Federation Proc. 23:327, 1964; Bergstrom, et al., 1965, op. cit.; Carlson, et al., Acta Med. Scand. 183:423–430, 1968; and Carlson et al., Acta Physiol. Scand. 75:161–169, 1969.]

The PGA and PGE compounds and derivatives and salts thereof increase the flow of blood in the mammalian kidney, thereby increasing volume and electrolyte content of the urine. For that reason, the compounds are useful in managing cases of renal disfunction, especially in cases of severely impaired renal blood flow, for example, the hepatorenal syndrome and early kidney transplant rejection. In cases of excessive or inappropriate ADH (antidiuretic hormone; vasopressin) secretion, the diuretic effect of these compounds is even greater. In anephretic states, the vasopressin action of these compounds is especially useful. Illustratively, the compounds are useful in alleviating and correcting cases of edema resulting from massive surface burns, in the management of shock, etc. For these purposes, the compounds are preferably first administered by intravenous injection at a dose in the range 10 to 1000 µg. per kg. of body weight or by intravenous infusion at a dose in the range 0.1 to 20 µg. per kg. of body weight per minute until the desired effect is obtained. Subsequent doses are given by intravenous, intramuscular, or subcutaneous injection or infusion in the range 0.05 to 2 mg. per kg. of body weight per day.

The PGE compounds, especially $PGE_1$, are useful in the treatment of psoriasis (Ziboh, et. al., Nature, 254, 351 (1975)). For this purpose, the compound is administered topically at a dose of 1–500 µg. 1 to 4 times daily until the desired effect is obtained.

The PGE, especially $PGE_2$, $PGF_\alpha$, and $PGF_\beta$ compounds are useful in the induction of labor in pregnant female animals, including man, cows, sheep, and pigs, at or near term [Karim et al., J. Obstet. Gynaec. Brit. Cwlth., 77:200–210, 1970] or in the induction of therapeutic abortion [Bygdeman et al., Contraception, 4, 293 (1971)]. For this purpose, the compound is infused intraveneously at a dose of 0.01 to 50 µg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. Alternative routes of administration are oral, extraamniotic or intraamniotic.

The PGE, $PGF_\alpha$, and $PGF_\beta$ compounds are useful for fertility control in female mammals [Karim, Contraception, 3 173 (1971] including humans and animals such as monkeys, rates, rabbits, dogs, cattle, and the like. By the term ovulating female mammals is meant animals which are mature enough to ovulate but not so old that regular ovulation has ceased. For that purpose, $PGF_{2\alpha}$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

Patents have been obtained for several prostaglandins of the E and F series as inducers of labor in mammals (Belgian Patent 754,158 and West German Pat. No. 2,034,641), and on $PGE_1$, $F_2$ and $F_3$ for control of the reproductive cycle (South African Patent 69/6089). It has been shown that luteolysis can take place as a result of administration of $PGF_{2\alpha}$ [Labhsetwar, Nature, 230, 528 (1971)] and hence prostaglandins have utility for fertility control by a process in which smooth muscle stimulation is not necessary.

The PGE and $PGF_2$ compounds are useful as antiarrhythmic agents (Forster, et al, Prostaglandins, 3, 895 (1973)). For this purpose the compound is infused intravenously at a dose range of 0.5–500 µg/kg/minute until the desired effect is obtained.

As mentioned above, the PGE compounds are potent antagonists of epinephrine-induced mobilization of free fatty acids. For this reason, these compounds are useful in experimental medicine for both in vitro and in vivo studies in mammals, including man, rabbits, and rats intended to lead to the understanding, prevention, symptom alleviation, and cure of diseases involving abnormal lipid mobilization and high free fatty acid levels, e.g., diabetes mellitus, vascular diseases, and hyperthyroidism.

The PGE and PGB compounds promote and accelerate the growth of epidermal cells and keratin in animals, including humans, useful domestic animals, pets, zoological specimens, and laboratory animals. For that reason, these compounds are useful in promoting healing of skin which has been damaged, for example, by burns, wounds, and abrasions, surgery, etc. These compounds are also useful in promoting adherence and growth of skin autografts, especially small, deep (Davis) grafts which are intended to cover skinless areas by subsequent outward growth rather than initially, and to retard rejection of homografts.

To promote the growth of epidermal cells, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, such as when there is substantial fluid loss as in the case of extensive burns or skin loss due to other causes, systemic administration is advantageous. Expecially in topical applications, these prostaglandins may be advantageously combined with antibiotics such as gentamycin, neomycin, polymyxin B, bacitracin, spectinomycin, tetracycline and oxytetracycline; with other antibacterials such as mafenide hydrochloride, sulfadiazine, furazolium chloride, and nitrofurazone; and with corticosteroids such as hydrocortisone, prednisolone, methylprednisolone, and fluprednisolone, each being used in the combination at the usual concentration suitable for its use alone.

In the preparation of synthetic pharmaceutical agents, among the principal objects is the development of analogs of naturally occurring compounds which are highly selective in their physiological activity and which have an increased duration of activity. In a series of compounds like the naturally-occurring prostaglandins which has an extremely broad activity spectrum, increasing the selectivity of a single compound usually involves the enhancement of one physiological effect and the diminution of the others. By increasing the selectivity, one would, in the case of the natural prostaglandins, expect to alleviate the severe side effects, particularly the gastrointestinal one frequently observed following systemic administration of the natural prostaglandinds.

In order to achieve increased selectivity and duration of action in the prostaglandin series, many researchers have concentrated on the molecular modification of the last five carbons of the methyl-terminated side chain. One modification consists of removing one to four carbon atoms from the end of the lower side chain and terminating the chain with an aryl or heteroaryl group. Compounds of this type are described, for instance, in Belgian Pat. No. 802,231. The 11-desoxy analogs of the natural prostaglandins have been described, for instance, in the published Dutch Pat. No. 16,804, Belgian Pat. No. 766,521 and the West German Offenlegungsschrift No. 2,103,005.

The 13,14-dehydro analogs of the naturally occurring PGE$_2$'s and PGF$_2$'s are known and their total synthesis by routes differing from those described herein have been described [Fried et al., *Annals, N.Y. Academy of Sciences*, 180, 38 (1971) and the references cited therein].

The West German Offenlegungsschift No. 2,357,781 describes a series of 13,14-acetylenic PGE and PGF analogs which have a trifluoromethyl group and also a five to ten carbon alkyl or alkenyl group at the 15-position. Additionally, intermediates of the structure

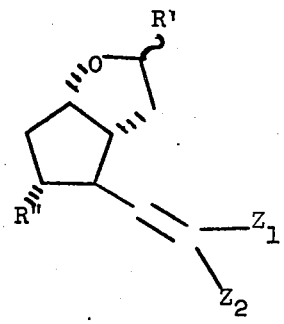

and

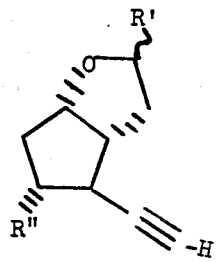

in which R' and R'' are free or etherized hydroxyl and one of $Z_1$ and $Z_2$ is hydrogen and the other is halogen. The balance of the lower side chain is added by metallizing the alkynyl compound and reacting it with a ketone of the structure $CF_3(C=O)R_6$ in which $R_6$ is a five to ten carbon alkyl or alkenyl radical.

Netherlands Pat. No. 73/05304 discloses a series of prostaglandins of the structure

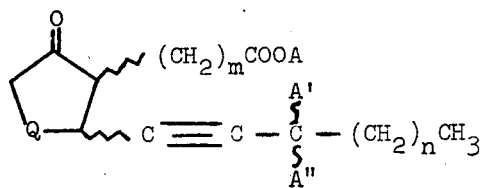

in which Q is among others methylene, hydroxy or tetrahydropyranyloxy-methylene; A is hydrogen or alkyl of one to seven carbon atoms; A' is hydrogen or alkyl of one to four carbon atoms; A'' is hydroxy, tetrahydropyranyloxy, alkoxyalkyloxy or trialkylsiloxy all of one to seven carbon atoms; m is 6 or 7; and n is an integer of from two to eight. These compounds differ from the compounds of the present invention in both structure and function. The compounds of the present invention have four carbon atoms in the straight part of the lower chain which is terminated by a phenyl or naphthyl groups; those of the prior art have from six to twelve carbon atoms in a chain terminated by a methyl group. Furthermore, the compounds of the present invention are useful as hypotensive and antiulcer agents whereas those of the prior art are used in the treatment of ulcers and the control of fertility.

SUMMARY OF THE INVENTION

In accordance with the present invention there are provided optically active compounds of the structure

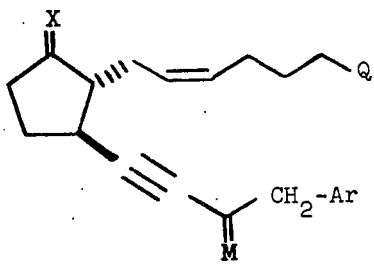

their optical antipodes and racemic mixtures thereof. X and M are selected from the group consisting of keto,

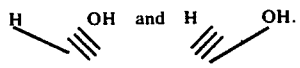

The bond in the 5-position is a cis double bond. Q is selected from the group consisting of tetrazol-5-yl and

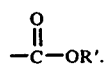

Ar is selected from the group consisting of phenyl, monosubstituted phenyl α- and β-furyl, α- and β-thienyl and α- and β-naphthyl. R' is selected from the group consisting of hydrogen, alkyl of from one to ten carbon atoms, aralkyl of from seven to nine carbon atoms, cycloalkyl of from three to eight carbon atoms, phenyl, monosubstituted phenyl and α- and β- naphthyl. The substituent on said monosubstituted phenyls is selected from the group consisting of fluoro, chloro, bromo, trifluoromethyl, phenyl, lower alkyl and lower alkoxy. The pharmaceutically acceptable salts of the acids are also described.

The preferred structures are

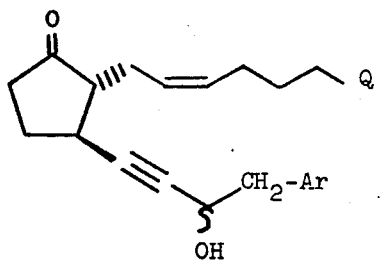

and

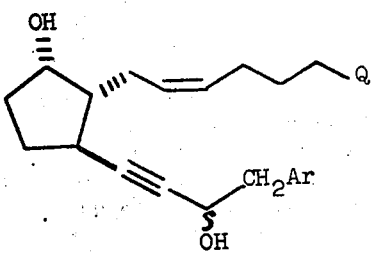

in which the wavy line indicates that the hydroxyl group in the 15-position may be attached in either the α- or β-position.

Among the possible R', hydrogen and p-biphenyl are preferred. Phenyl and β-naphthyl are preferred as Ar.

Of special interest are the 9-oxo-11-desoxy-15-hydroxy-16-phenyl-ω-tetranorprosta-cis-5-ene-13-yneoic acids and their p-biphenyl esters. These compounds are extremely useful as antihypertensive agents as evidenced by their ability to lower systemic blood pressure. This effect was observed in dogs.

The compounds of the present invention also exhibit anti-ulcer activity. This effect is observed in rats receiving oral doses of the order of 1.0 mg.

It has also been found that compounds of the structure

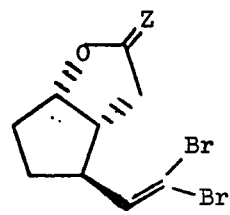

and

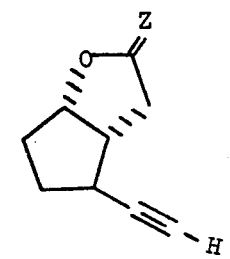

and their optical antipodes and racemic mixtures thereof wherein Z is selected from the group consisting of keto,

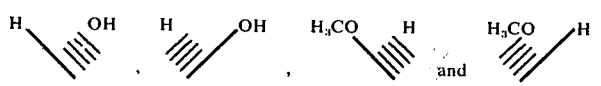

are valuable as synthetic intermediates in the preparation of prostaglandins having an acetylenic bond between $C_{13}$ and $C_{14}$. These compounds are, of course, also useful in producing precursors of the above-mentioned 13,14-acetylenic prostaglandins.

A process has also been found for producing the above-mentioned intermediates from the known compound, 2-[5α-hydroxy-2β-(aldehydo)cyclopent-1α-yl]acetic acid, γ-lactone (Corey and Ravindranathan, *Tetrahedron Lett.*, 1971, 4753). The process comprises contacting carbon tetrabromide with triphenylphosphine in the approximate molar ratio of one to two in a reaction-inert solvent until the reaction to form the phosphorane or ylide is substantially complete. The γ-lactone is then added to the reaction mixture to form the corresponding 2β-(2,2-dibromovinyl) compound. This is then converted to the γ-hemiacetal by the known reduction with a metal hydride which does not reduce olefinic bonds. Among the useful hydrides is diisobutylaluminum hydride. The hemiacetal is then converted to the γ-methylacetal in the usual manner and this compound is converted to the corresponding 2β-ethynyl compound by contacting it with a strong base such as n-butyl lithium, t-butyl lithium or phenyllithium in reaction-inert solvent at a temperature below about −60°C., allowing the reaction mixture to warm to ambient temperature and then quenching the mixture in water.

Reaction Scheme A

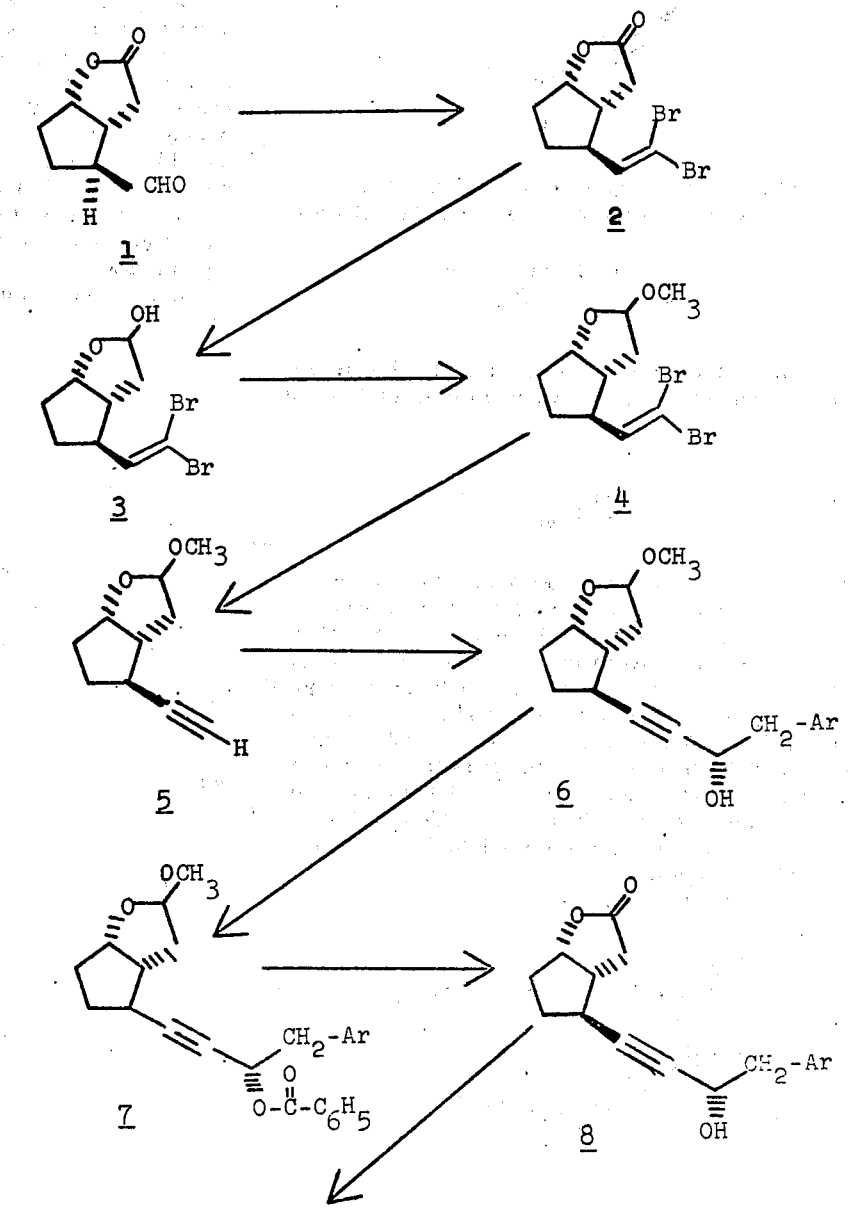

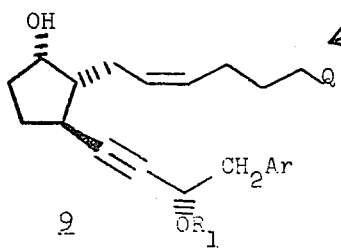

DETAILED DESCRIPTION OF THE INVENTION

As shown in Reaction Scheme A, the first step (1 → 2) is a Wittig-type condensation between the known aldehyde 1 (cf. Corey and Ravindranathan, supra) and triphenyltribromomethylphosphonium bromide to form the 2β-(2,2-dibromovinyl) compound 2. In the usual Wittig reaction, the reactive phosphorane or ylide is formed by the reaction of the phosphonium salt with a strong base such as n-butyllithium and the aldehyde is then added to the reaction mixture to form the Wittig condensation product. In the present case, however, carbon tetrabromide is contacted with approximately double the number of moles of triphenylphosphine in a reaction-inert solvent such as substantially anhydrous methylene chloride under an inert atmosphere until the reaction to form the phosphorane is substantially complete. Reaction-inert solvents and also atmospheres those which are substantially free of adverse effects on reactants and products under the conditions employed. In the present case, the phosphorane is formed when the excess triphenylphosphine reacts with the phosphonium salt. A redox mechanism is probably operative here though such a mechanism is not necessary for the proper operation of the process. The aldehyde 1 is then added and the mixture stirred until the reaction to form 2-[5α-hydroxy-2β-(2,2-dibromovinyl)cyclopent-1α-yl] acetic acid, γ-lactone 2 is substantially complete. The product is isolated by precipitation with a non-polar hydrocarbon solvent such as pentane or petroleum ether. The insoluble fraction is separated and reworked with a polar solvent such as methylene chloride followed by precipitation with the non-polar solvent for a number of cycles. The product 2 is isolated evaporating the combined non-polar fractions and it may be purified by solid-liquid chromatography on an adsorbent such as silica gel.

(2 → 3) is a reduction of the lactone 2 to the hemiacetal 3 using a suitable reducing agent such as diisobutyl aluminum hydride in a reaction-inert solvent. This reduction yields a mixture of epimers which need not be resolved. The β-epimer is shown. Low reduction temperatures are preferred and −60° to −80°C. are usual. However, higher temperatures may be employed if over reduction does not occur. 3 is then purified by column chromatography.

(3 → 4) involves the conversion of the hemiacetal 3 to the methylacetal 4. This is accomplished by dissolving 3 in anhydrous methanol in the presence of a catalyst such as boron trifluoride etherate. The product is recovered by evaporation, dilution with ether, extraction with brine, drying with a desiccant such as sodium sulfate and finally another evaporation.

(4 → 5) involves the conversion of the 2,2-dibromovinyl group to an ethynyl group. This is accomplished by treating the compound with at least two equivalents of a strong organometallic base such as n-butyllithium or phenyllithium in reaction-inert solvent such as substantially anhydrous tetrahydrofuran until the reaction is substantially complete. Low temperatures are preferred and about −60° to about −80°C. are usual. The reaction mixture is quenched in water. The crude product is recovered as in (3 → 4) above and it is then distilled to afford the pure product.

(5 → 6) involves contacting 5 in reaction-inert solvent such as substantially anhydrous tetrahydrofuran under an inert atmosphere in the presence of a strong organometallic base such as n-butylithithium with an aldehyde of the structure ArCH$_2$CHO wherein Ar is selected from the group consisting of phenyl, monosubstituted phenyl α- and β-furyl, α- and β-thienyl and α- or β-naphthyl. The monosubstituent is selected from the group consisting of fluoro, chloro, bromo, trifluoromethyl, phenyl, lower alkyl and lower alkoxy. Any of the Ar groups with the scope of the present invention may be used here. 5 and the base are slowly mixed at about 0°C. and cooled to about −60° to −80°C. before the aldehyde is added slowly. The reaction mixture is poured into water and extracted with ether. The ether extract is dried and evaporated to yield the crude product 6 which may be purified by chromatography on silica gel. This reaction produces an epimeric mixture of 3α- and 3β-hydroxy compounds. Only the α-epimer is shown. If desired, the mixture may be resolved at this point by high pressure liquid chromatography as described below. If the mixture is resolved and the remainder of the synthesis carried out on a particular epimer, the final prostaglandin analog will have the identical configuration at the 15-position to the epimer of 6 which was used, unless of course, the hydroxy group is oxidized to a keto group.

(6 → 7) requires the esterification of the 3-hydroxy group by contacting it with benzoyl chloride in reaction-inert solvent such as methylene chloride in the presence of a base such as pyridine. The reaction mixture is stirred under an inert atmosphere such as dry nitrogen until the reaction is substantially complete. The reaction mixture is poured into water and extracted several times with ether. The extracts are combined and washed with cold, dilute hydrochloric acid. The ether layer is then dried and evaporated to yield 7.

In (7 → 8), the first step is the conversion of the methylacetal 7 to the hemiacetal. This is accomplished by solvolyzing the methylacetal in a solvent such as 1:1 water/tetrahydrofuran in the presence of a mineral acid such as hydrochloric acid at ambient temperatures. The hemiacetal is recovered by ether extraction, drying and evaporation. The hemiacetal is then converted to the lactone by oxidation with a reagent which oxidizes hydroxyl groups but not carbon-carbon unsaturated bonds. Jones reagent is usually preferred [Fieser and Fieser, *Reagents for Organic Synthesis*, Wiley (New York, 1967), pp. 142–143.]. The product is recovered by dilution with water extraction with ether, drying the extract and evaporation. The crude product may be purified by column chromatography to yield the substantially pure 3-benzoyl protected γ-lactone. Alternatively, the 3-benzoyl protected γ-lactone may be prepared directly from 7 by the action of the Jones' reagent. The benzoxy group is removed by solvolyzing the compound in substantially anhydrous methanol in the presence of substantially anhydrous potassium carbonate under an inert atmosphere at ambient temperatures. The product 8 is isolated by acidifying the reaction mixture to a pH of about 3 with hydrochloric acid, diluting with water and extracting with ether. The ether extract is washed with brine dried with a desiccant such as sodium sulfate and evaporated to yield crude 8 which may be purified by column chromatography.

In (8 → 9), the first step involves the protection of the 3-hydroxy group by contacting 8 with a slight molar excess of 2,3-dihydropyran in reaction-inert solvent such as methylene chloride at about 0°C. under an inert atmosphere in the presence of added p-toluenesulfonic acid monohydrate. The crude product is recovered by pouring the reaction mixture into ether, washing with saturated sodium bicarbonate and then brine, drying and evaporation. This crude product is then converted to the γ-hemiacetal by reduction as described above with diisobutylaluminum hydride. The product is then isolated and purified by column chromatography as described above. To convert the γ-hemiacetal to 9, it is contacted with an ylide. The ylide is formed from (4-carbohydroxy-n-butyl)triphenylphosphonium bromide with sodium methylsulfinylmethide in a molar ratio of about one-to-two in a reaction-inert solvent such as dry dimethylsulfoxide under an inert atmosphere at about 40°C. To this reaction mixture containing the ylide, the γ-hemiacetal is slowly added. After about one hour, the reaction is quenched in ice water and covered with a layer of ethyl acetate. The solution is then extracted several times with ethyl acetate and the combined organic extracts are washed with brine, dried with sodium sulfate and evaporated to a solid residue which is titurated with ether and filtered. The filtrate is then concentrated, purified by column chromatography and evaporated to yield 9. The tetrazolyl analogs of the present invention may be prepared by using the ylide of (4-(2-tetrzaol-5-yl)butyl) triphenyl-phosphonium bromide in the above described reaction.

As shown in Reaction Scheme B, 9 may be converted to the corresponding 15α-hydroxy PGE$_2$ analog 12 by first oxidizing the 9α-hydroxy moiety to a keto group by treating it with Jones reagent and isolating the product as described above. This 9-oxa-15α-tetrahydropyran-2-yloxy compound is then hydrolyzed to a 15α-hydroxy compound for instance by dissolving in a 65:35 mixture of glacial acetic acid:water under an inert atmosphere and stirring at about room temperature until the reaction is substantially complete. The mixture is then evaporated and chromatographed on silica gel to yield substantially pure 12.

As also shown in Reaction Scheme B, 9 may be converted to the corresponding 15α-hydroxy PGF$_{2\alpha}$ 10. This is accomplished by the glacial acetic acid:water hydrolysis described in the reaction series (9 → 12) above.

12 may be converted to the corresponding 15 keto-PGE$_2$ 11 by treating it with at least about one equivalent of Jones reagent or another reagent which oxidizes hydroxy groups but not double or triple bonds. Alternatively, 10 may be treated at least about two equivalents of Jones reagent to afford 11.

9 → 13 involves acylation of 9 at the 9-position with acetic anhydride and pyridine to form an acetate intermediate. Other blocking groups may be used provided the group is stable to mild acid hydrolysis. Such groups include alkanoyl of from 2 to 9 carbons, phenalkanoyl of up to 10 carbons, benzoyl, tolyl, p-phenylbenzoyl, or α- or β-naphthoyl. The protecting group at C$_{15}$ is then removed as described above to provide a second intermediate. The next step involves oxidation of the C$_{15}$ alcohol moiety to provide a third intermediate. Any reagent capable of oxidizing hydroxyl groups which does not attack double bonds may be used, however, the Jones' reagent is usually preferred. The last step in this sequence involves transesterification of the protecting group at C$_9$.

Reaction Scheme B

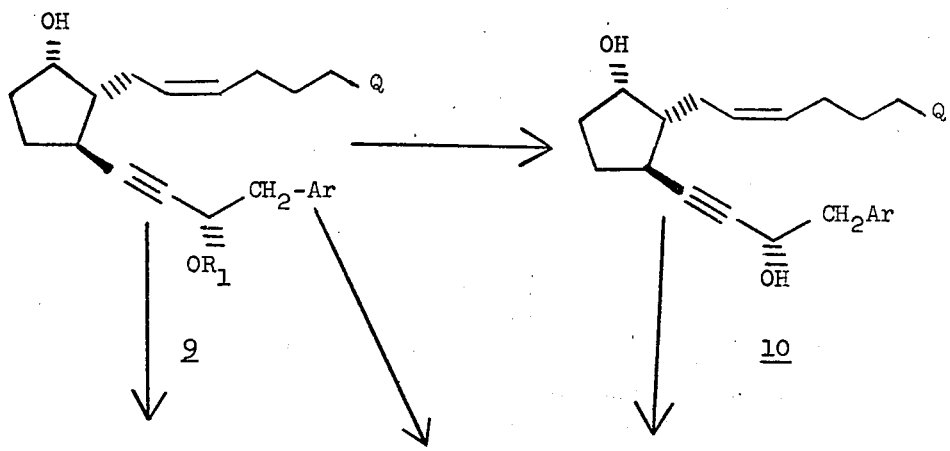

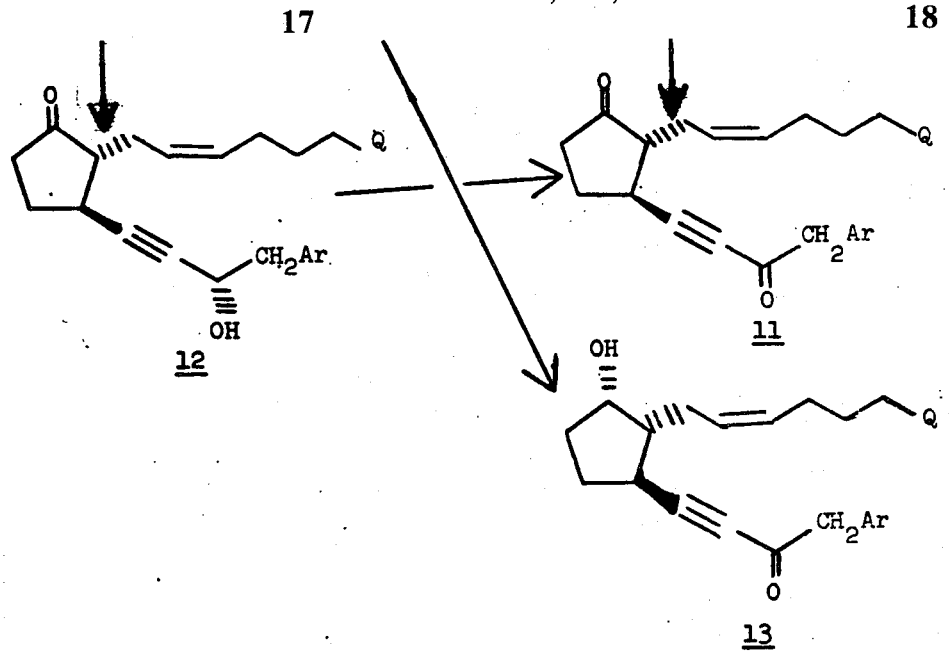

This is usually done by treatment with anhydrous potassium carbonate in an alcoholic solvent such as methanol, which affords the 15-keto F$_2$ $_\beta$ analogs of this invention.

The assignment of the configuration at C$_{15}$ is made on the basis of mobilites in thin layer chromatography of the alcohols 8 and C$_{15}$-epi-8. It is assumed that the less polar (higher R$_f$) epimer has the 15α-hydroxy configuration and the more polar (lower R$_f$) epimer has the 15β-hydroxy configuration. Among the suitable solvent systems are mixtures of ether or ethyl acetate in benzene. This assignment of C$_{15}$ configuration is based on that observed for the synthesis of the natural prostaglandins (Corey, et. al., J. Am. Chem. Soc., 93, 1491 (1971) ).

Phenyl and substituted phenyl esters of the present invention are prepared by contacting a prostanoic acid with an appropriate phenol in reaction-inert solvent such as dry methylene chloride in the presence of a coupling agent such as dicyclohexylcarbondiimide or diethylcarbodiimide. For instance, ent-9-oxo-11-desoxy-15β-hydroxy-16-phenyl-ω-tetranorprosta-cis-5-ene-13-yneoic acid may be contacted with p-phenylphenol in dry methylene chloride in the presence of dicyclohexylcarbodiimide to form the corresponding ester. Alkyl and phenalkyl esters of the present invention may be prepared by contacting a prostanoic acid with an appropriate diazoalkane in a reaction-inert solvent such as ether or tetrahydrofuran. Alternatively, the esters of the present invention may be prepared by first contacting a prostanoic acid with pivaloyl chloride in a reaction inert solvent such as ether in the presence of an appropriate base such as triethylamine and then treating the resultant intermediate with an appropriate alcohol.

In the foregoing procedures, where purification by column chromatography is desired, appropriate chromatographic supports include neutral alumina and silica gel. The chromatography is suitably conducted in reaction-inert solvents such as ether, ethyl acetate, benzene, chloroform, methylene chloride, cyclohexane and n-hexane, as further illustrated in the appended examples. Where purification by high pressure liquid chromatography is desired, appropriate supports include 'Corasil', 'Porasil', and 'Lichrosorb' with inert solvents such as ether, chloroform, methylenechloride, cyclohexane and n-hexane being employed.

It will be seen that the foregoing formulae depict optically active compounds. It is intended that both optical antipodes, e.g. 8,12-nat and 8,12-ent, be embraced by the foregoing formulae and in the appended claims. The two optical antipodes are readily prepared by the same methods by mere substitution of the appropriate optically active precursor aldehyde. It will be clear however, that the corresponding racemates will exhibit valuable biological activity by virtue of their content of the above-mentioned biologically active optical isomers, and it is intended that such racemates also be embraced by the foregoing formulae herein and in the appended claims. The racemic mixtures are readily prepared by the same methods employed herein to synthesize the optically active species, by mere substitution of corresponding racemic precursors in place of optically active starting materials.

In numerous in vivo and in vitro tests we have demonstrated that the new prostaglandin analogs possess physiological activities comparable but much more tissure selective and longer acting than those exhibited by the natural prostaglandins (see above). These tests include, among others, a test for effect on dog blood pressure, inhibition of stress-induced ulceration in the rat, effect on mouse diarrhea, inhibition of stimulated gastric acid secretion in rats and dogs, spasmogenic effect on isolated guinea pig and rat uterus, protective effect on histamine induced bronchospasm in the guinea pig, and antifertility activity in rats and guinea pigs.

The physiological responses observed in these tests are useful in determining the utility of the test substance for the treatment of various natural and pathological conditions. Such determined utilities include: vasodilator activity, antihypertensive activity, bronchodilator activity, antiarrythmic activity, cardiac stimulant activity, antifertility activity and antiulcer activity.

An advantage possessed by 11-desoxy prostaglandins of the E series in general is their increased stability as compared with such as PGE$_2$. In addition the novel 11-desoxy-16-aryl-ω-tetranorprostaglandins of this invention possess highly selective activity profiles compared with the corresponding naturally occurring prostaglandins and, in many cases, exhibit longer duration of action. The novel prostaglandin analogs of this invention, especially the 16-phenyl compounds, possess useful antihypertensive activity. At the same time, other physiological activities are markedly depressed in comparison with $PGE_2$. Especially useful in this regard are the 9-oxo-11-desoxy-15-hydroxy-16-phenyl-ω-tetranorprosta-cis-5-ene-13 yneoic acids and their p-biphenyl esters. In addition, these compounds exhibit a high degree of antiulcer activity. The 16-phenyl and β-naphthyl compounds are especially useful for the treatment of peptic ulcers.

Pharmacologically acceptable salts of the acids of this invention useful for the purposes described above are those with pharmacologically acceptable metal cations, ammonium, amine cations, or quaternary ammonium cations.

Especially preferred metal cations are those derived from the alkali metals, e.g., lithium, sodium and potassium and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives therof, e.g., 1-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglucamine, N-methylglucosamine, epherdrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

The new compounds of this invention can be used in a variety of pharmaceutical preparations which contain the compound or a pharmaceutically acceptable salt thereof, and they may be administered in the same manner as natural prostaglandins by a variety of routes, such as intravenous, oral and topical, including aerosol, intrivaginal, and intranasal, among others.

The 16-phenyl-ω-tetranorprostaglandin analogs and their p-biphenyl esters of the present invention are useful as hypotensive agents. They may be administered systemically or preferably intravenously at a dose level of 0.01 to about 1.0 mg/kg of body weight per day.

The 16-aryl-ω-tetranorprostaglandin analogs of the present invention and their esters are also useful antiulcer agents. For treatment of peptic ulcers these drugs may be administered orally in the form of capsules or tablets at doses of 0.01 to 1.0 mg/kg per day.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol and other known carriers for medicaments. If desired, these pharmaceutical compositions may contain auxiliary substances such as preserving agents, wetting agents, stabilizing agents, or other therapeutic agents such as antibiotics.

The following examples are merely illustrative, and in no way limit the scope of the appended claims. In these examples it will be appreciated that all temperatures are expressed in Centigrade, all melting and boiling points are uncorrected.

EXAMPLE I

2-[5α-Hydroxy-2β-(2,2-dibromovinyl)cyclopent-1α-yl]acetic acid, γ-lactone (2)

To a solution of 138 g (0.528 mole) triphenylphosphine in 800 ml of anhydrous methylene chloride at 0° in a dry nitrogen atmosphere was added in one portion of a solution of 87.3 g (0.264 mole) carbon tetrabromide in 100 ml of anhydrous methylene chloride. The resulting bright orange solution was stirred for 5 minutes. A solution of 20.4 g (0.132 mole) 2-[5α-hydroxy-2β-(aldehydo)cyclopent-1α-yl]acetic acid, γ-lactone (1) in 100 ml of anhydrous methylene chloride was then added over 2 minutes via an addition funnel. After stirring for an additional 4 minutes, the reaction was diluted with 5 liters of pentane and filtered to remove insoluble material. The insoluble fraction was reworked by additional cycles of methylene chloride extraction and pentane precipitation to remove all the olefinic product. The combined pentane fractions were evaporated to yield 90 g (>100%) crude 2-[5α-hydroxy-2β-(2,2-dibromovinyl)cyclopent-1α-yl]acetic acid, γ-lactone (2). The product was purified by chromatography on 700 g of silica gel (Baker "Analyzed" reagent 60–200 mesh). The yield of pure 2-[5α-hydroxy-2β-(2,2-dibromovinyl)cyclopent-1α-yl]acetic acid, γ-lactone (2) was 28.7 g (70%).

The n.m.r. spectrum ($CDCl_3$) exhibited a doublet 6.40δ(1H) for the vinyl hydrogen, a broad singlet at 5.05δ(1H) and multiplets at 2.40–3.20δ(4H) and 1.25–2.40δ(4H) for the remaining protons. The ir ($CHCl_3$) spectrum had a strong absorbtion at 1770 $cm^{-1}$ for the γ-lactone carbonyl.

EXAMPLE II

2-[5α-Hydroxy-2β-(2,2-dibromovinyl)cyclopent-1α-yl]acetaldehyde, γ-hemiacetal (3)

A solution of 28.7 g (92.6 mmole) 2-[5α-hydroxy-2β-(2,2-dibromovinyl)-cyclopent-1α-yl]acetic acid, γ lactone (2) in 700 ml dry toluene was cooled to −78° in a dry nitrogen atmosphere. To this cooled solution was added 114 ml (92.6 mmole) of 20% diisobutylaluminum hydride in n-hexane (Alfa Inorganics) dropwise at such a rate that the internal temperature remained below −66°. After 10 minutes of stirring at −78°, the reaction was diluted with 2.5 liters of ether, washed with 50% sodium potassium tartrate solution (2 × 200 ml), dried (MgSO₄) and concentrated to yield 28.1 g 2-[5α-hydroxy-2β-(2,2-dibromovinyl)cyclopent-1α-yl]acetaldehyde, γ-hemiacetal (3).

EXAMPLE III

2-[5α-Hydroxy-2β-(2,2-dibromovinyl)cyclopent-1α-yl]acetaldehyde, γ-methylacetal (4)

To a solution of 28 g (90 mmole) 2-[5α-hydroxy-2β(2,2-dibromovinyl)-cyclopent-1α-yl]acetaldehyde, γ-hemiacetal (3) in 500 ml of anhydrous methanol under a dry nitrogen atmosphere at 25° was added 40 drops boron trifluoride etherate. After stirring 25 minutes, the reaction was quenched with 40 ml of saturated aqueous sodium bicarbonate solution. The reaction was evaporated to a volume of 75 ml, diluted with 1 liter of ether. The ether layer was washed with brine (2 × 100 ml), dried over Na₂SO₄ and evaporated to yield 30 g (>100%) of crude 2-[5α-hydroxy-2β-(2,2-dibromovinyl)cyclopent-1α-yl]-acetaldehyde, γ-methylacetal (4).

EXAMPLE IV

2-[5α-Hydroxy-2β-ethynyl cyclopent-1α-yl]acetaldehyde, γ-methylacetal (5)

A solution of 30.0 g (92 mmole) 2-[5α-hydroxy-2β-(2,2-dibromovinyl)-cyclopent-1α-yl]acetaldehyde, γ-methylacetal (4) in 500 ml of anhydrous tetrahydrofuran was cooled to −78° in a dry nitrogen atmosphere. To this cooled solution was added dropwise 92 ml (202 mmole) of 2.2M butyl lithium (Alfa Inorganics) at such a rate that the internal temperature remained below −60° (15 minutes). The reaction was stirred for 2 hours at −78° and 1 hour at 25° then quenched with 200 ml ice water and extracted with ether (2 × 300 ml). The combined ether extracts were washed with brine, dried (Na₂SO₄) and evaporated to yield 15.8 g crude 2-[5α-hydroxy-2β-ethnyl cyclopent-1α-yl]acetaldehyde, γ-methylacetal (5). The product was purified by distillation yielding 12.9 g (60% from (1)) pure 2-[5α-hydroxy-2β-ethnyl cyclopent-1α-yl]acetaldehyde, γ-methylacetal (5), b.p. 55–65° at 0.15 mm.

The nmr spectrum (CCl₄) exhibited a doublet 4.85δ(1H) for the acetal proton, a doublet 3.16δ(3H) for the methoxy protons a multiplet 4.30–4.78δ(1H) and a multiplet 1.30–3.00δ(9H) for the remaining protons. The ir (CCl₄) spectrum had a strong absorbtion 3320 cm⁻¹ for the acetylene.

EXAMPLE V

2-[5α-Hydroxy-2α-(3-hydroxy-4-phenyl-1-butynyl)cyclopent-1α-yl]acetaldehyde, γ-methylacetal (6)

A solution of 2.51 g (15.1 mmole) 2-[5α-hydroxy-2β-ethynyl cyclopent-1α-yl]acetaldehyde, γ-methylacetal (5) in 125 ml of anhydrous tetrahydrofuran was cooled to 0° in a dry nitrogen atmosphere. To this cooled solution was added dropwise (over 10 minutes) 8.9 ml (22.7 mmole) 2.2M butyl lithium in n-hexane (Alfa Inorganics). The resulting yellow solution was stirred at 0° for 20 minutes then cooled to −78°. A solution of 2,68 g (22.7 mmole) phenylacetaldehyde in 5 ml of anhydrous tetrahydrofuran was then added dropwise at such a rate that the internal temperature remained below −66° (10 min). After stirring for 1 hour at −78°, the reaction was poured onto water, extracted with ether, dried (Na₂SO₄) and evaporated to yield 5.7 g crude 2-[5α-hydroxy-2β-(3-hydroxy-4-phenyl-1-butynyl)cyclopent-1α-yl]acetaldehyde, γ-methylacetal (6) which was purified by column chromotography on 250 g silica gel (Baker "Analyzed" Reagent 60–200 mesh). After elution of less polar impurities the product 3.0 g (70%) was collected.

The nmr spectrum (CDCl₃) exhibited a singlet at 7.30δ(5H) for the phenyl protons, a doublet at 4.95δ(1H) for the acetal proton, a singlet at 3.32δ(3H) for the methoxy protons, a doublet at 2.94δ(2H) for the benzyl protons a multiplet 4.29–4.90δ(2H) and a multiplet 3.20–1.20δ(8H) for the remaining protons. The i.r. (CCl₄) spectrum absorbtion at 3600 cm⁻¹ for the hydroxyl.

6 is an epimeric mixture of 3α- and 3β-hydroxy compounds which was not resolved. The synthesis was carried forward with this mixture so that the prostaglandin products are mixtures of 15α- and 15β-hydroxy epimers.

Other 2-arylacetaldehydes (for example see below) may be substituted for the phenylacetaldehyde used above to generate the corresponding 2-[5α-hydroxy-2β-(3-hydroxy-4-aryl-1-butynyl) cyclopent-1α-yl]acetaldehyde, γ-methacetals.

m-tolylacetaldehyde
o-tolylacetaldehyde
p-tolylacetaldehyde
p-diphenylacetaldehyde
(a-naphthyl) acetaldehyde
(m-trifluoromethylphenyl) acetaldehyde
(p-trifluoromethylphenyl) acetaldehyde (o-flourophenyl) acetaldehyde
(m-fluorophenyl) acetaldehyde
(p-fluorophenyl) acetaldehyde
(m-chlorophenyl) acetaldehyde
(p-bromophenyl) acetaldehyde
(p-methoxyphenyl) acetaldehyde
p-(t-butyl)phenyl) acetaldehyde

EXAMPLE VI

2-[5α-Hydroxy-2β-(3-benzoyloxy-4-phenyl-1-butynyl)cyclopent-1α-yl]acetaldehyde, γ-methylacetal (7)

To a solution of 3 g (10.5 mmole) 2-[5α-hydroxy-2β-(3-hydroxy-4-phenyl-1-butynyl)cyclopent-1α-yl]acetaldehyde, γ-methylacetal (6) in 32 ml of anhydrous methylene chloride containing 21 ml of pyridine was added in one portion 2.22 g (15.8 mmole benzoyl choloride. The reaction was stirred at room temperature in a dry nitrogen atmosphere for 2 hours, then poured onto water (150 ml) and extracted with ether (2 × 500 ml). The combined ether extracts were washed with cold 10% aqueous hydrochloric acid to remove the pyridine. The ether layer was then dried (Na₂SO₄) and evaporated to yield 4.3 g crude 2-[5α-hydroxy-2β-(3-benzoyloxy-4-phenyl-1-butynyl)cyclopent-1α-yl]acetaldehyde, γ-methylacetal (7).

In a similar manner the other compounds of Example V may be converted into the corresponding benzoyloxy derivative.

EXAMPLE VII

2-[5α-Hydroxy-2β-(3-benzoyloxy-4-phenyl-1-butynyl)cyclopent-1α-yl]acetaldehyde, γ-hemiacetal.

A solution of 4.3 g crude 2-[5α-hydroxy-2β-(3-benzoyloxy phenyl-1-butynyl)cyclopent-1α-yl]acetaldehyde, γ-methyacetal (7) in 1 l. of aqueous tetrahydrofuran (50/50 water/tetrahydrofuran) containing 40 drops of concentrated hydrochloric acid was stirred at room temperature during 96 hours, then extracted with ether (2 × 500 ml). The combined ether extracts were evaporated to remove most of the tetrahydrofuran. The residue (100 ml) was diluted with benzene, dried (Na$_2$SO$_4$) and evaporated to yield 4.3 g crude 2-[5α-hydroxy-2β-(3-benzoyloxy-4-phenyl-1-butynyl)cyclopent-1α-yl]acetaldehyde, γ-hemiacetal.

In a similar manner the other compounds of Example VI may be converted into the corresponding γ-hemiacetal derivatives

EXAMPLE VIII

2-[5α-Hydroxy-2β-(3-benzoyloxy-4-phenyl-1-butynyl)cyclopent-1α-yl]acetic acid, γ-lactone.

A solution of 4.3 g crude 2-[5α-hydroxy-2β-(3-benzoyloxyl-4-phenyl-1-butynyl)-cyclopent-1α-yl]acetaldehyde, γ-hemiacetal in 200 ml of acetone was cooled to 0° in a dry nitrogen atmosphere. To this cooled solution was added dropwise (over 5 min.) 3.9 ml (10.5 mmole) of 2.67 M Jones reagent. After stirring for 45 min. at 0°, the reaction was diluted with water (200 ml) and extracted with ether (3 × 300 ml). The combined ether extracts were dried (Na$_2$SO$_4$) and evaporated to yield 4.4 g crude 2-[5α-hydroxy-2β-(3-benzoyloxy-4-phenyl-1-butynyl)cyclopent-1α-yl] acetic acid, γ-lactone. The product was purified by column chromatography on 250 g silica gel (Baker "Analyzed" Reagent 60–200 mesh). The yield of pure 2-[5α-hydroxy-2β-(3-benzoxy-4-phenyl-1-butynyl)-cyclopent-1α-yl]acetic acid, γ-lactone was 3.5 g (90% from (6)).

The n.m.r. spectrum (CDCl$_3$) exhibited a mulitplet at 7.68–7.10δ(8H) and multiplet at 7.80–8.18δ(2H) for the phenyl protons, a doublet at 3.14δ(2H) for the benzyl hydrogens a triplet at 5.79δ(1H), a multiplet at 5.00–4.66δ(1H) and a multiplet at 2.98–1.44δ(8H) for the remaining protons. The ir (CHCl$_3$) had strong absorbtion at 1720 cm$^{-1}$ and 1770 cm$^{-1}$ for the ester and lactone respectively.

In a similar manner the other compounds of Example VII may be converted to the corresponding γ-lactone derivatives.

EXAMPLE IX

2-[5α-Hydroxy-2β-(3-hydroxy-4-phenyl-1-butynyl)cyclopent-1α-yl]acetic acid, γ-lactone (8).

To a solution of 3.5 g (9.37 mmole) 2-[5α-hydroxy-2β-(3-benzoyloxy-4-phenyl-1-butynyl)cyclopent-1α-yl]acetic acid, γ-lactone in 70 ml of anhydrous methanol was added 1.29 g anhydrous powdered potassium carbonate. After stirring at room temperature in a dry nitrogen atmosphere for 2 hrs, the reaction was cooled to 0° and acidified to pH 3 with 1N hydrochloric acid. After stirring for 10 minutes the reaction was diluted with water (150 ml) and extracted with ether (2 × 300 ml). The combined ether extracts were washed with brine, dried (Na$_2$SO$_4$) and evaporated to yield 3.6 g crude 2-[5α-hydroxy-2β-(3-hydroxy-4-phenyl-1-butynyl)cyclopent-1α-yl]acetic acid, γ-lactone (8). The product was purified by column chromatography on 125 g silica gel (Baker "Analyzed" Reagent 60–200 mesh). The yield of pure 2-[5α-hydroxy-2β-(3-hydroxy-4-phenyl-1-butynyl)cyclopent-1α-yl]acetic acid, γ-lactone (8) was 2.3 g (91%).

The n.m.r. spectrum (CDCl$_3$) was exhibited a singlet at 7.28δ(5H) for the phenyl protons, a doublet at 2.94δ(2H) for the benzyl protons a multiplet at 4.77δ(1H), a triplet at 4.54δ(1H), and a multiplet at 2.80–140δ(8H) for the remaining protons. The i.r. spectrum (CHCl$_3$) had strong absorbtion at 1770 cm$^{-1}$ for the lactone carbonyl and absorbtion at 3600 cm$^{-1}$ for the hydroxyl.

In a similar manner the other compounds of Example VIII may be converted into the corresponding hydroxy γ-lactone derivatives.

EXAMPLE X

2-[5α-Hydroxy-2β-(3-{tetrahydropyran-2-yloxy}-4-phenyl-1-butynyl) cyclopent-1α-yl]acetic acid, γ-lactone.

To a solution of 2.3 g (8.52 mmole) 2-[5α-hydroxy-2β-(3-hydroxy-4-phenyl-1-butynyl)cyclopent-1α-yl]acetic acid, γ-lactone (8) in 70 ml anhydrous methylene chloride containing 0.79 g (9.4 mmole) of 2,3-dihydropyran at 0° in a dry nitrogen atmosphere was added 35 mg p-toluenesulfonic acid monohydrate. After stirring for 40 minutes at 0°, the reaction was poured onto ether (300 ml). The ether solution was washed with saturated sodium bicarbonate (1 × 50 ml) then saturated brine (1 × 30 ml), dried (Na$_2$SO$_4$) and concentrated to yield 2.8 g crude 2-[5α-hydroxy-2β-(3-{tetrahydropyran-2-yloxy}-4-phenyl-1-butynyl) cyclopent-1α-yl]acetic acid γ-lactone.

In a similar manner the other compounds of Example IX may be converted into the corresponding tetrahydrophran-2-yloxy γ-lactone derivatives.

EXAMPLE XI

2-[5α-Hydroxy-2β-(3-{tetrahydropyran-2-yloxy}-4-phenyl-1-butynyl) cyclopent-1α-yl]acetaldehyde, γ-hemiacetal.

A solution of 2.74 g (7.75 mmole) 2-[5α-hydroxy-2β-(3-{tetrahydropyran-2-yloxy}-4-phenyl-1-butynyl)-cyclopent-1α-yl]acetic acid in 50 ml anhydrous toluene was cooled to −78° in a dry nitrogen atmosphere. To this cooled solution was added 10.7 ml (8.52 mmole) of 20% diisobutylaluminum hydride in n-hexane (Alfa Inorganics) dropwise at such a rate that the temperature remained below −66° (over 20 minutes). After an additional 45 minutes of stirring at −78°, the reaction was diluted with ether (300 ml). The ether solution was washed with 50% sodium potassium tartrate solution (2 × 150 ml), dried (MgSO$_4$) and concentrated to yield 3.0 g crude 2-[5α-hydroxy-2β-(3-{tetrahydropyran-2-yloxy}-4phenyl-1-butynyl)cyclopent-1α-yl acetaldehyde, γ-hemiacetal (12), which was purified by column chromatography on 120 g of silica gel (Baker "Analyzed" Reagent). The yield of pure 2-[5α-hydroxy-2β-(3-{tetrahydropyran-2-yloxy}-4-phenyl-1-butynyl)-cyclopent-1α-yl]acetaldehyde, γ-hemiacetal was 2.03 g.

In a similar manner the other compounds of Example X may be converted into the corresponding tetrahydropyran-2-yloxy γ-hemiacetal derivatives.

EXAMPLE XII

9α-Hydroxy-15-(tetrahydropyran-2-yloxy)-16-phenyl-ω-tetranorprosta-cis-5ene-13-yneoic acid (9).

To a solution of 6.20 g (14 mmole) (4-carbohydroxy-n-butyl) triphenylphosphonium bromide in 20 ml of dry dimethyl sulfoxide in a dry nitrogen atmosphere was added 11.7 ml (26.6 mmole) of a 2.27M solution of sodium methylsulfinylmethide. To this red ylide solution at 40° (oil bath) was added dropwise a solution of 1.65 g (4.65 mmole) 2-[5α-hydroxy-2β-(3-{tetrahydropyran-2-yloxy}-4-phenyl-1-butynyl)cyclopent-1α-yl]acetaldehyde, γ-hemiacetal in 15 ml of dry dimethylsulfoxide over a period of 10 minutes. After 45 minutes at 40°, the reaction was poured onto ice water. The basic aqueous solution (200 ml) was covered with ethyl acetate (200 ml) and with vigorous stirring was acidified to pH∼3 with 1N aqueous hydrochloric acid. The acidic solution was extracted with ethyl acetate (2 × 100 ml) and the combined organic extracts washed with saturated brine, dried ($Na_2SO_4$) and evaporated to a solid residue which was triturated with ether and filtered. The filtrate was concentrated and purified by column chromatography on 250 g silica gel (Baker "Analyzed" Reagent 60–200 mesh). After removal of high $R_f$ impurities, 1.7 g of 9α-hydroxy-15-(tetrahydropyran-2-yloxy)-16-phenyl-ω-tetranor-prosta-cis-5-ene-13-yneoic acid (9) was collected.

The n.m.r. spectrum ($CDCl_3$) exhibited a singlet at 7.34δ(5H) for the phenyl protons, a multiplet at 5.65–5.25δ(2H) for the olefinic protons, a doublet at 3.03δ(2H) for the benzylic protons, and a broad singlet at 6.32δ(2H); mulitplets at 5.20–5.00δ(1H), 4.75–4.32δ(1H) and 4.30–4,04δ(1H and 3.80–1.20δ(20H) for the remaining protons.

In a similar manner the other compounds of Example XI may be converted into the corresponding 9α-hydroxy-15-(tetrahydropyran-2-yloxy)-16-aryl-ω-tetranorprosta-cis-5-ene-13-yneoic acid.

The products of this example (9) may be converted by the procedures of Examples XXX-XXXIV into the 15-keto 11-desoxy $PGF_2 \alpha$ analogs of this invention. In addition, the product of this example (9) may be hydrolyzed by the procedure of Example XXVI into the 11-desoxy $PGF_2 \alpha$ analogs of this invention. The 11-desoxy $PGF_2 \alpha$ analogs thereby prepared may be converted into the corresponding esters of this invention by the procedures of Examples XV, XXVII, and XXVIII.

EXAMPLE XIII

9-OxO-15-(tetrahydropyran-2-yloxy)-16-phenyl-ω-tetranor-prosta-cis-5-ene-13-yneoic acid To a solution of 990 mg (2.25 mmole) 9α-hydroxy-15-tetrahydropyran-2-yloxy-16-phenyl-ω-tetranor-prosta-cis-5-ene-13-yneoic acid (9) in 45 ml of acetone at −10° in a dry nitrogen atmosphere was added 0.91 ml (2.47 mmole) of 2.67 M Jones' reagent. After 10 minutes at −10°, the reaction was poured onto ethyl acetate (350 ml), washed with water (2 × 50 ml), dried ($Na_2SO_4$) and concentrated to yield 933 mg crude 9-oxO-15-(tetrahydropyran-2-yloxy)-16-phenyl-ω-tetranor-prosta-cis-5-ene-13-yneoic acid.

In a similar manner the compounds of Example XII may be converted into the corresponding 9-oxo derivatives.

EXAMPLE XIV

9-Oxo-15-hydroxy-16-phenyl-ω-tetranor-prosta-cis-15-ene-13-yneoic acid (12).

A solution of 933 mg (2.2 mmole) 9-oxo-15-tetrahydropyran-2-yloxy-16-phenyl-ω-tetranor-prosta-cis-5-ene-13-yneoic acid in 50 ml. of a 65:35 mixture of glacial acetic acid:water was stirred under nitrogen at 27° for 3 days, then concentrated by rotary evaporation. The resultant crude oil was purified by chromatography on 65 g silica gel (Mallinckrodt CC-7 100–200 mesh). After elution of less polar impurities the 9-oxo-15-hydroxy-16-phenyl-ω-tetranor-prosta-15-ene-13-yneoic acid (12) weighing 450 mg was collected.

The n.m.r. spectrum ($CDCl_3$) exhibited a singlet at 7.30δ(5H) for the phenyl protons, a broad singlet at 6.56δ(2H) for the acid and hydroxy protons, a multiplet at 5.55–5,23δ(2H) for the olefinic protons, a doublet at 2.94δ(2H) for the benzylic protons a triplet at 4.59δ(1H), and a multiplet 2.80–1.30δ(14H) for the remaining protons. The i.r. spectrum ($CHCl_3$) had absorbtion at 1700 $cm^{-1}$ and 1730 $cm^{-1}$ for the carboxylic acid and ketone respectively.

In a similar manner the compounds of Example XIII may be converted into the 11-desoxy $PGF_2$ analogs of the present invention.

EXAMPLE XV 9-oxo-15-hydroxy-16-phenyl-ω-tetranor-prosta cis-5-ene-13-yneoic acid, p-biphenyl ester.

To a solution of 106 mg. (.3 mmole) 9-oxo-15-hydroxy-16-phenyl-ω-tetranor-prosta-cis-5-ene-13-yneoic acid and 510 mg (3mmole) pγbiphenyl alchol in 30 ml of methylene chloride is added 93 mg (0.45 mmole) dicyclohexyl-carbodiimide. After stirring, for 18 hr at room temperature the soln is concentrated by rotary evaporation and purified by column chromatography on silica gel (Baker "Analyzed" Reagent). After elution of less polar impurities the 9-oxo-15-hydroxy-16-phenyl-ω-tetranor-prosta-cis-5-ene-13-yneoic acid, p-biphenyl ester is collected.

In a similar fashion, the compounds of Examples XIV, XXV, XXVI, XXX and XXIV may be converted to an ester in which R′ may be phenyl, monosubstituted phenyl or α- or β-naphthyl. The monosubstituent may be fluoro, chloro, bromo, trifluoromethy, phenyl, lower alkyl or lower alkoxy.

EXAMPLE XVI

2-[5α-Hydroxy-2β-(3-hydroxy-4-(β-naphthyl)-1-butynyl)cyclopent-1α-yl]acetaldehyde, γ-methylacetal (6).

A solution of 2.32 g (14 mmole) 2-[5α-hydroxy-2β-ethynyl cyclopent-1α-yl]acetaldehyde, γ-methylacetal (5) in 125 ml of anhydrous tetrahydrofuran was cooled to 0° in a dry nitrogen atmosphere. To this cooled solution was added dropwise (over 10 minutes) 9.1 ml (21 mmole) 2.2 M butyl lithium in n-hexane (Alfa Inorganics). The resulting yellow solution was stirred at 0° for 20 minutes then cooled to −78°. A solution of 3.6 g (21 mmole) naphthylacetaldehyde in 15 ml of anhydrous tetrahydrofuran was added dropwise at such a rate that the internal temperature remained below −66° (over 10 minutes). After stirring for 1 hour at −78°, the reaction was poured onto water, extracted with ether, dried ($Na_2SO_4$) and evaporated to yield 6.2 g crude 2-[5α-hydroxy-2β-(3-hydroxy-4-(β-naphthyl)-1-butynyl) cyclopent-1α-yl]acetaldehyde, γ-methylacetal (6) which was purified by column chromatography on 300 g of silica gel (Baker "Analyzed" Reagent 60–200 mesh). After elution of less polar impurities the product, 2.53 g, was collected.

The n.m.r. spectrum exhibited a mulitplet at 8.20–7.10 σ (7H) for the naphthyl protons, a singlet at 3.26σ(3H) for the methoxy protons, a multiplet at 5.09–4.28σ(3H), a doublet at 3.40σ(2H) and a multiplet at 3.80–1.10σ(8H) for the remaining protons. The i.r. (CHCl₃) had absorbtion and 3600 cm⁻¹ for the hydroxyl.

EXAMPLE XVII

2-[5α-Hydroxy-2β-(3-benzoyloxy-4-(β-naphthyl)-1-butynyl)cyclopent-1α-yl]acetaldehyde, γ-methylacetal (7).

To a solution of a 2.75 g (8.2 mmole)2-[5α-hydroxy-2β-(3-hydroxy-4-(β-naphthyl)-1-butynyl)cyclopent-1α-yl]acetaldehyde, γ-methylacetal (6) in 24 ml of anhydrous methylene chloride containing 16 ml of pyridine was added in one portion 1.72 g (12.3 mmole) benzoyl chloride. The reaction was stirred at room temperature in a dry nitrogen atmosphere for 2 hours, then poured onto water (150 ml) and extracted with ether (2 × 300 ml). The combined ether extracts were washed with cold 10% aqueous hydrochloric acid to remove the pyridine. The ether layer was then dried (Na₂SO₄) and evaporated to yield 4.1 g crude 2-[5α-hydroxy-2β-(3-benzoyloxy-4-(β-naphthyl)-1-butynyl)-cyclopent-1α-yl]acetaldehyde, γ-methylacetal (7).

EXAMPLE XVIII

2-[5α-Hydroxy-2β-(3-benzoyloxy-4-(β-naphthyl)-1-butynyl)cyclopent-1α-yl]acetaldehyde, γ-hemiacetal.

A solution of 4.1 g crude 2-[5α-hydroxy-2β-(3-benzoyloxy-4-(β-naphthyl)-1-butynyl)cyclopent-1α-yl]acetaldehyde, γ-methylacetal (7) in 1 l. of aqueous tetrahydrofuran (50/50 water/tetrahydrofuran) containing 40 drops of concentrated hydrochloric acid was stirred at room temperature overnight then extracted with ether (2 × 500 ml). The combined ether extracts were evaporated to remove most of the tetrahydrofuran. The residue (100 ml) was diluted with benzene, dried (Na₂SO₄and evaporated to yield 4.4 g crude 2-[5α - hydroxy - 2β - (3 - benzoyloxy - 4 - (β - naphthyl) - 1-butynyl)cyclopent-1α-yl]acetaldehyde, γ-hemiacetal.

EXAMPLE XIX

2[5α-Hydroxy-2β-(3-benzoyloxy-4-(β-naphthyl)-1-butynyl)cyclopent-1α-yl]acetic acid, γ-lactone.

A solution of 4.4 g crude 2-[5α-hydroxy-2β-(3-benzoyloxy-4-(β-naphthyl)-1-butynyl)-cyclopent-1α-yl]acetaldehyde, γ-hemiacetal in 200 ml of acetone was cooled to 0° in a dry nitrogen atmosphere. To this cooled solution was added dropwise (over 5 minutes) 37 ml (0.01 mmole) of 2.67 M Jones Reagent. After stirring for 45 minutes at 0°, the reaction was diluted with water (200 ml) and extracted with ether (3 × 300 ml). The combined ether extracts were dried (Na₂SO₄) and evaporated to yield 4.4 g crude 2-[5α-hydroxy-2β-(3-benzoyloxy-4-(β-naphthyl)-1-butynyl)cyclopent-1α-yl]acetic acid, γ-lactone. The product was purified by column chromatography on 250 g silica gel (Baker "Analyzed Reagent" Reagent 60—200 mesh). The yield of pure 2-[5α-hydroxy-2β-(3-benzoxy-4-napthyl-1-butynyl)-cyclopent-1α-yl]acetic acid, γ-lactone was 3.90 g.

The n.m.r. spectrum (CDCl₃) exhibited a multiplet at 3.40–7.15 σ (12H) for the phenyl and naphthyl protons, a triplet at 6.00 σ (1H), a multiplet at 4.91–4.64 σ (1H), a multiplet at 4.00–3.20 σ (2H) and a multiplet at 3.80–1.40 σ (8H) for the remaining protons. The i.r. spectrum (CHCl₃) had strong absorbtion at 1770 cm⁻¹ and 1750 cm⁻¹ for the lactone and ester respectively.

EXAMPLE XX

2-[5α-Hydroxy-2β-(3-hydroxy-4-(β-naphthyl)-1-butynyl)cyclopent-1α-yl]acetic acid, γ-lactone (8).

To a solution of 3.09 g (6.8 mmole) 2-[5α-hydroxy-2β-(3-benzoyloxy-4-(β-naphthyl)-1-butynyl)cyclopent-1α-yl]acetic acid, γ-lactone in 70 ml of anhydrous methanol was added 0.94 g (6.8 mmole) anhydrous powdered potassium carbonate. After stirring at room temperature in a dry nitrogen atmosphere for 2 hours, the reaction was cooled to 0° and acidified to pH~3 with 1N hydrochloric acid. After stirring for 10 minutes the reaction was diluted with water (150 ml) and extracted with ether (2 × 300 ml). The combined ether extracts were washed with brine, dried (Na₂SO₄) and evaporated to yield 3.0 g crude 2-[5α-hydroxy-2β-(3-hydroxy-4-(β-naphthyl)-1-butynyl)cyclopent-1α-yl]acetic acid, γ-lactone (8). The product was purified by column chromatography on 125 g silica gel (Baker "Analyzed" Reagent 60–200 mesh). The yield of pure 2-[5α-hydroxy-2β-(3-hydroxy-4-(β-naphthyl)-1-butynyl)cyclopent-1α-yl]acetic acid, γ-lactone (8) was 1.83 g.

The i.r. spectrum (CHCl₃) had strong absorbtion at 1770 cm⁻¹ for the lactone carbonyl and absorbtion at 3600 cm⁻¹ for the hydroxyl.

EXAMPLE XXI

2-[5α-Hydroxy-2β-(3-{tetrahydropyran-2-yloxy}-4-(β-naphthyl)-1-butynyl)cyclopent-1α-yl]acetic acid, γ-lactone.

To a solution of 1.83 g. (5.17 mmole) 2-[5α-hydroxy-2β-(3-hydroxy-4-(β-naphthyl)-1-butynyl)cyclopent-1α-yl]acetic acid, γ-lactone (8) in 30 ml anhydrous methylene chloride containing 0.70 ml (7.7 mmole) of 2,3-dihydropyran at 0° in a dry nitrogen atmosphere was added 15 mg p-toluenesulfonic acid monohydrate. After stirring for 40 minutes at 0°, the reaction was poured onto ether (300 ml). The ether solution was washed with saturated sodium bicarbonate (1 × 40 ml), then saturated brine (1 × 30 ml), dried (Na₂SO₄) and concentrated to yield 2.15 g crude 2-[5α-hydroxy-2β-(3-{tetrahydropyran-2-yloxy}-4-(β-naphthyl)-1-butynyl)cyclopent-1α-yl]acetic acid γ-lactone.

EXAMPLE XXII

2-[5α-Hydroxy-2β-(3-{tetrahydropyran-2-yloxy}-4-(β-naphthyl)-1-butynyl)cyclopent-1α-yl]acetaldehyde, γ-hemiacetal.

A solution of 2.45 g (5.6 mmole) 2-[5α-hydroxy-2β-(3-{tetrahydropyran-2-yloxy}-4-(β-naphthyl)-1-butynyl)cyclopent-1α-yl]acetic acid in 40 ml anhydrous toluene was cooled to −78° in a dry nitrogen atmosphere. To this cooled solution was added 7.75 ml (6.2 mmole) of 20% disobutyl-aluminum hydride in n-hexane (Alfa Inorganics) dropwise at such a rate that the temperature remained below −66° (over 20 minutes). After an additional 45 minutes of stirring at −78°, the reaction was diluted with ether (300 ml). The ether solution was washed with 50% sodium potassium tartrate solution (2 × 150 ml), dried (MgSO₄) and concentrated to yield 2.5 g crude 2-[5α-hydroxy-2β-(3-{tetrahydropyran-2-yloxy}-4-(β-naphthyl)-1-butynyl)cyclopent-1α-yl]acetaldehyde, γ-hemiacetal, which was purified by column chromatography on 100 g of silica gel (Baker "Analyzed" Reagent). The yield of pure 2-[5α-hydroxy-2β-(3-{tetrahydropyran-2-yloxy}4-(β-naphthyl)-1-butynyl)-cyclopent-1α-yl]acetaldehyde, γ-hemiacetal was 2.03 g.

EXAMPLE XXIII

9α-Hydroxy-15-(tetrahydropyran-2-yloxy)-16-(β-naphthyl)-ω-tetranor-prosta-cis-5-ene-13-yneoic acid (9).

To a solution of 6.13 g (13.8 mmole) 4-carbohydroxy-n-butyl) triphenyl-phosphonium bromide in 35 ml of dry dimethyl sulfoxide in a dry nitrogen atmosphere was added 12.8 ml (26.2 mmole) of a 2.05 M solution of sodium methylsulfinylmethide. To this red ylide solution at 40° (oil bath) was added dropwise a solution of 2.01 g (4.5 mmole) 2-[5α-hydroxy-2β-(3-{tetrahydropyran-2-yloxy}-4-(β-naphthyl)-1-butynyl)-cyclopent-1α-yl]acetaldhyde, γ-hemiacetal in 15 ml of dry dimethylsulfoxide over a period of 10 minutes. After 45 minutes at 40°, the reaction was poured onto ice water. The basic aqueous solution (200 ml) was covered with ethyl acetate (200 ml) and with vigorous sitrring was acidified to pH~3 with 1N aqueous hydrochloric acid. The acidic solution was extracted with ethyl acetate (2 × 100 ml) and the combined organic extracts washed with saturated brine, dried ($Na_2SO_4$) and evaporated to a solid residue which was triturated with ether and filtered. The filtrate was concentrated and purified by column chromatography on 250 g silica gel (Baker "Analyzed" Reagent 60—200 mesh). After removal of high $R_f$ impurities, 1.7 g of 9α-hydroxy-15-(tetrahydropyran-2-yloxy)-16-(β-naphthyl)-ω-tetranor-prosta-cis-5-ene-13-yneoic acid (9) was collected.

EXAMPLE XXIV 9-(Oxo-15-(tetrahydropyran-2-yloxy)-16-(β-naphthyl)-ω-tetranor-prosta-cis-5-ene-13-yneoic acid.

To a solution of 1.15 g (2.1 mmole) 9α-hydroxy-15-(tetrahydropyran-2-yloxy)-16-(β-naptyl)-ω-tetranor-prosta-cis-5-ene-13-yneoic acid (9) in 25 ml of acetone, at −10° in a dry nitrogen atmosphere was added 0.89 ml (2.4 mmole) of 2.67 M Jones reagent. After 10 minutes at −10°, the reaction was poured onto ethyl acetate (150 ml), washed with water (2 × 50 ml), dried ($Na_2SO_4$) and concentrated to yield 1.16 mg crude 9-oxa-15-(tetrahydropyran-2-yloxy)-16-(β-naphthyl)-ω-tetranor-prosta-cis-5-ene-13-yneoic acid.

EXAMPLE XXV

9-Oxo-15-hydroxy-16-(β-naphthyl)-ω-tetranor-prosta-15-ene-13-yneoic acid (12).

A solution of 480 mg 9-oxo-15-(tetrahydropyran-2-yloxy)-16-(β-naphthyl)-ω-tetranor-prosta-cis-5-ene-13-yneoic acid in 20 ml of a 65::35 mixture of glacial acetic acid::water was stirred under nitrogen at 27° overnight, then concentrated by rotary evaporation. The resultant crude oil was purified by chromatography on 50 g silica gel (Mallinckrodt CC-7 100–200 mesh). After elution of less polar impurities the 9-oxo-15-hydroxy-16-(β-naphthyl)-ω-tetranor-prosta-15-ene-13-yneoic acid (12weighing 124 mg was collected.

The n.m.r. spectrum ($CDCl_3$) exhibited a multiplet at 8.20–7.19 σ (7H) for the naphthyl protons, a singlet at 6.66 σ (2H) for the hydroxyl and acid protons, a multiplet at 5.30 σ (2H), a singlet at 3.80 σ (1H), a doublet at 3.43 σ (2H) and a multiplet at 2.80–1.10 σ (14H) for the remaining protons.

EXAMPLE XXVI

9α-Hydroxy-15-hydroxy-16-(β-naphthyl)-ω-tetranor-prosta-cis-5-ene-13-yneoic acid (10).

A solution of 400 mg (0.817 mmole) 9α-hydroxy-15-(tetrahydropyran-2-yloxy-16-(β-naphthyl)-ω-tetranor-prosta-cis-5-ene-13-yneoic acid (9) in 20 ml of a 65::35 mixture of glacial acetic acid:: water was stirred under nitrogen at 27° overnight, then concentrated by rotary evaporation. The resultant oil was purified by chromatography on 35 g of silica gel (Mallinckrodt CC-7 100 –200 mesh). After elution of less polar impurities the 9α-hydroxy-15-hydroxy-16-(β-naphthyl)-ω-tetranor-prosta-15-ene-13-yneoic acid (10) weighing 148 mg was collected.

In a similar manner the compounds of Example XXIII may be converted into the 11-desoxy $PGF_2$ α analogs of the present invention.

EXAMPLE XXVII 9-oxo-15-hydroxy-16-phenyl-ω-tetranor-prosta-cis-5-ene-13-yneoic acid, methyl ester.

To a solution of 106 mg (0.3 mmole) 9-oxo-15-hydroxy-16-phenyl-ω-tetranor-prosta-cis-5-ene-13-yneoic acid in 20 ml of ether is added a ethereal solution of diazamethane generated from 100 mg (0.68 mmole) N-Methyl-$N^1$-nitro-N nitrosoguanidine. After stirring for 5 minutes at room temperature, acetic acid is added to destroy excess diazomethane. The ether solution was then washed with sodium bicarbonate (1 × 20 ml) water (1 × 20 ml) and dried ($Na_2SO_4$). The solution is concentrated by rotary evaporation to afford the 9-oxo-15-hydroxy-16-phenyl-ω-tetranor-prosta-cis-5-ene-13-yneoric acid, methyl ester.

In a similar fashion, the compounds of Examples XIV, XXV, XXVI, XXX and XXXIV may be converted to an ester in which $R^1$ may be alkyl of from one to ten carbon atoms or aralkyl of from seven to nine carbon atoms.

EXAMPLE XXVIII 9-oxo-15-hydroxy-16-phenyl-ω-tetranor-prosta-cis-5-ene-13-yneoic acid, cyclohexyl ester.

To a solution of 65 mg. 9-oxo-15-hydroxy-16-phenyl-ω-tetranor-prosta-cis-5-ene-13-yneoic acid in 3 ml of methylene chloride is added 21 mg of triethylamine. After 5 minutes 25 mg of pivaloyl chloride is added then stirred for an additional 10 minutes. A 0.2 ml portion of cyclohexanol and 0.3 ml of pyridine is added then stirred at room temperature for 2 hours. The reaction is then diluted with ethyl acetate and the organic layer is washed with water, dried ($MgSO_4$) and concentrated. Purification of the crude residue by silica gel chromatography provides, after removal of less polar impurities, the title compound.

In a similar fashion, the compounds of Examples XIV, XXV, XXVI, XXX, and XXXIV may be converted to an ester in which $R^1$ may be alkyl of from one to ten carbon atoms, aralkyl of from seven to nine carbon atoms, phenyl, memosubstituted phenyl or α- or β-naphthyl. The menosubstituent may be fluoro, chloro, bromo, trifluoromethyl, phenyl, lower alkyl or lower alkory.

EXAMPLE XXIX

2-Descarboxy-2-(Tetrayol-5-yl)-9-hydroxy-15-(tetrahydropyian-2-yloxy) 16-phenyl-cis-5-ω-tetranor-prosten-13-ynoic acid.

To a solution of 2.42 g (5.16 mmoles) of 4-(tetrayol-5-yl) butyltriphenylphosphonium bromide in 20 ml dry dimethylsulfoxide in a dry nitrogen atmosphere is added 4.2 ml of a 2.2 M solution of sodium methylsulfinyl-methide in dimethylsulfoxide. To the red ylide solution is added dropwise a solution of 500 mg (1.3 mmoles) 2-[5-Hydroxy-2β-(3-{tetra-hydropyran-2-yloxy}-4-phenyl-1-butynyl) cyclopent-1α-yl]acetaldehyde, γ-hemiacetal in 6 ml of dimethylsulfoxide over a period of 5 minutes. After an additional 1 hour stirring at room temperature, the reaction mixture is poured into ice water. The basic aqueous solution is acidified to PH~3 and extracted with ethyl acetate (3 × 75 ml). The organic extracts are evaporated to a solid residue. This solid residue is triturated with ethyl acetate and the filtrate concentrated to yield 2-descarboxy-2-(tetrazol-5-yl)-9-hydroxy-15-(tetrahydropyran-2-yloxy)-16-phenyl-cis-5-ω-tetranor-prosten-13-ynoic acid which is purified by column chromatography. After elution of less polar impurities, the desired product is collected.

In a similar manner the compounds of Examples XI and XXII may be converted into the corresponding tetrazol-5yl-derivatives.

The product of this example may be converted into the 11-desoxy $PGF_2$ and $PGF_2$ α tetrazol analogs of the present invention by the procedures of Examples XXIV - XXVI and XXX - XXXIV.

EXAMPLE XXX 9,15-Dioxo-16-phenyl-ω-tetranor-prosta-cis-5-ene-13-ynoic acid:

To a solution of 356 mg (1 mmole) 9α,15-dihydroxy-16-phenyl-ω-tetranor-prosta-cis-5-ene-13-ynoic acid in 30 ml of acetone, at 10° in a dry nitrogen atmosphere is added 0.89 ml (2.4 mmole) of 2.67 M Jones reagent. After 10 minutes at −10°, the reaction is poured onto ethyl acetate (100 ml), washed with water (2 × 50 ml), dried ($Na_2SO_4$) and concentrated to yield 360 mg crude 9,15-dioxo-16-phenyl-ω-tetranor-prosta-cis-5-ene-13-ynoic acid which is purified by column chromatography on silica gel (Baker "Analyzed" Reagent). After removal of less polar impurities the product is collected.

In a similar fashion the compounds of Examples XIV, XV, XXV, XXVI, XXVII and XXVIII may be converted into the corresponding 11-desoxy-15-keto $PGF_2$ analogs of the present invention.

EXAMPLE XXXI

9α-Acetoxy-15-(tetrahydropran-2-yloxy)-16-phenyl-ω-tetranor-prosta-cis-5-ene-13-ynoic acid.

To a solution containing 2 ml pyridine, 2 ml acetic anhydride and 10 ml of methylene chloride is added, in one portion, a solution of 440 mg (1 mmole) 9α-hydroxy-15-(tetrahydropyran-2-yloxy)-16-phenyl-ω-tetranor-prosta-cis-5-ene-13-ynoic acid in 2 ml of methylene chloride. After stirring for 1 hour at room temperature the reaction is diluted with ether (100 ml). The ethereal layer is washed with 1 W hydrochloric acid (2 × 20 ml), water (2 × 20 ml), dried ($Na_2SO_4$), then concentrated by rotary evaporation to afford 9α-acetoxy-15-(tetrahydropyran-2-yloxy)-16-phenyl-ω-tetranor-prosta-cis-5-ene-13-ynoic acid which was used without further purification.

In a similar manner the compounds of Examples XII, XXIII, and XXIX may be converted into the corresponding acetoxy derivative.

EXAMPLE XXXII

9α-Acetoxy-15-hydroxy-16-phenyl-ω-tetranor-prosta-cis-5-ene-yneoic acid.

A solution of 500 mg (1.1 mmole) 9α-acetoxy-15-(tetrahydropyran-2-yloxy)-16-phenyl-ω-tetranor-prosta-cis-5-ene-13-yneoic acid in 20 ml of a 65::35 mixture of glacial acetic acid::water is stirred under nitrogen at 27° overnight, then concentrated by rotary evaporation. The resultant oil is purified by chromatography on 35 g of silica gel (Baker "Analyzed" Reagent). After elution of less polar impurities the product, 9α-acetoxy-15-hydroxy-16-phenyl-ω-tetranor-prosta-cis-5-ene-13-yneoic acid was collected.

In a similar manner the compounds of Example XXXI may be converted into the corresponding hydroxy derivatives.

EXAMPLE XXXIII

9α-Acetoxy-15-oxo-16-phenyl-ω-tetranor-prosta-cis-5-ene-13-yneoic acid.

To a solution of 396 mg (1 mmole) 9α-acetoxy-15-hydroxy-16-phenyl-ω-tetranor-prosta-cis-5-ene-13-ynoeic acid in 20 ml of acetone at −10° in a dry nitrogen atmosphere is added 0.45 ml (1.2 mmole) of 2.67 M Jones reagent. After 10 minutes at −10°, the reaction is poured onto ethyl acetate (150 ml), washed with water (2 × 50 ml), dried ($Na_2SO_4$), and concentrated to give the crude 9α-Acetoxy-15-oxo-16-phenyl-ω-tetranor-prosta-cis-5-ene-13-yneoic acid which was used without further purification.

In a similar fashion the compounds of Examples XXXII may be converted to the corresponding oxo derivatives.

EXAMPLE XXXIV

9α-Hydroxy-15-oxo-16-phenyl-ω-tetranor-prosta-cis-5-ene-13-yneoic acid.

A solution of 300 mg (0.76 mmole) 9α-acetoxy-15-oxo-16-phenyl-ω-tetranor-prosta-cis-5-ene-13-yneoic acid in 20 ml of a 50::50 mixture of methanol-water containing 900 mg of sodium hydroxide is stirred at room temperature for 5 hours. The solution is neutralized with 1 N hydrochloric acid and concentrated by rotary evaporation to afford the crude 9α-hydroxy-15-oxo-16-yneoic acid which was purified by column chromatography on silica gel (Baker "Analyzed" Reagent). After elution of less polar impurities, the desired product was collected.

In a similar manner the compounds of Example XXXIII may be converted into the corresponding 11-desoxy-15-deto $PGF_2$ α analogs of the present invention.

EXAMPLE XXXV

2-[5α-Hydroxy-2β-(3-benzoyloxy-4-phenyl-1-butynyl)cyclopent-1α-yl]acetic acid, γ-lactone.

A solution of 4.5 g 2-[5α-hydroxy-2β-(3-benzoyloxy-4-phenyl-1-butynyl)cyclopent-1α-yl]acetaldehyde γ-methylacetal (7) in 200 ml of acetone was cooled to 0° in a dry nitrogen atmosphere. To this cooled solution was added dropwise (over 5 minutes) 4.0 ml of 2.67 M Jones reagent. After stirring for 1 hour at 0°, the reaction was diluted with water (200 ml) and extracted with ether (3 × 200 ml). The combined ether extracts were dried ($Na_2SO_4$) and evaporated to yield 4.3 g crude 25α-hydroxy-2β-(3-benzoyloxy-4-1-butynyl)cyclopent-1α-yl]acetic acid, γ-lactone. The product was purified by chromatograpny on 200g silica gel (Baker "Analyzed" Reagent 60–200 mesh). The yield of pure 2-[5α-hydroxy-2β-(3-benzoyloxy-4-phenyl-1-butynyl)-cylopent-1α-yl]acetic acid, γ-lactone was 3.7g.

The nmr spectrum ($CDCl_3$) exhibited a multiplet at 7.68–7.10 (8H) and a multiplet at 7.80–8.18 (2H) for the phenyl protons, a doublet at 3.14 (2H) for the benzyl hydrogens, a triplet at 5.79 (1H), a multiplet at 5.00–4.66 (1H) and a multiplet at 2.98–1.44 (8H) for the remaining protons. The ir($CHCl_3$) had strong absorbtion at 1720 $cm^{-1}$ and 1770 $cm^{-1}$ for the ester and lactone respectively.

In a similar manner the compounds of Example VI and XIII may be converted into corresponding γ-lactone.

What is claimed is:

1. An optically active compound of the structure

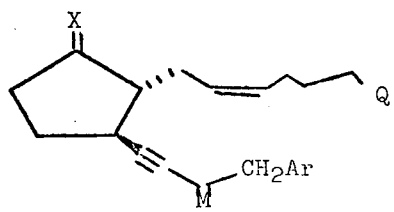

its optical antipode, the racemate thereof and the pharmaceutically acceptable salts of the acids wherein:
X and M are selected from the group consisting of keto

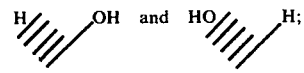

Q is tetrazol-5-yl and
Ar is selected from the group consisting of phenyl, α-naphthyl, β-naphthyl and monosubstituted phenyl, the substituents on said monosubstituted phenyl being selected from the group consisting of fluoro, chloro, bromo, trifluoromethyl, phenyl, lower alkyl and lower alkoxy.

2. A compound of claim 1 wherein Ar is phenyl.
3. A compound of claim 1 wherein Ar is β-naphthyl.
4. A compound of claim 1 wherein X is keto.

* * * * *